United States Patent [19]

Martin

[11] 4,307,075

[45] Dec. 22, 1981

[54] TOPICAL TREATMENT OF APHTHOUS STOMATITIS

[75] Inventor: Frederick H. Martin, West Chazy, N.Y.

[73] Assignee: American Home Products Corporation, New York, N.Y.

[21] Appl. No.: 225,175

[22] Filed: Jan. 15, 1981

Related U.S. Application Data

[63] Continuation of Ser. No. 74,609, Sep. 13, 1979, abandoned.

[51] Int. Cl.³ .................... A61F 13/00; A61L 15/03; A61K 9/70
[52] U.S. Cl. ...................................... 424/28; 128/268
[58] Field of Search ........................... 424/28; 128/268

[56] References Cited

U.S. PATENT DOCUMENTS

| | | | |
|---|---|---|---|
| 3,339,546 | 9/1967 | Chbn | 424/28 |
| 3,632,740 | 1/1972 | Robinson et al. | 424/28 |
| 3,696,811 | 10/1972 | Chbn | 424/28 |
| 3,769,071 | 10/1973 | Trancik | 424/28 |
| 3,896,789 | 7/1975 | Trancik | 424/28 |
| 3,972,995 | 8/1976 | Tsuk et al. | 424/28 |
| 4,073,291 | 2/1978 | Marvol et al. | 424/28 |
| 4,117,120 | 10/1978 | Elderbaum | 424/195 |

OTHER PUBLICATIONS

U.S. Pharmacist, Feb., 1978, pp. 36–48.
Arch. Dermatol, vol. 109, 400–402 (1974).
Oral Surgery, vol. 30, No. 4, 476–487 (1970).

Primary Examiner—Shep K. Rose
Attorney, Agent, or Firm—Adley F. Mandel

[57] ABSTRACT

A novel method of treating aphthous stomatitis, lesions, sores and blisters affecting the mucous membranes and surrounding areas comprising topical application of tape dosage forms containing minor amounts of topically effective active ingredients is disclosed.

6 Claims, No Drawings

TOPICAL TREATMENT OF APHTHOUS STOMATITIS

This is a continuation of application Ser. No. 74,609, filed Sept. 13, 1979, now abandoned.

BACKGROUND OF THE INVENTION

1. Field of the Invention

This invention relates to the treatment of blisters, sores, lesions and like irritations of the mucous membranes and applicators employed therewith. In particular the invention relates to the treatment of canker sores with minor amounts of a medicament localized on the source of irritation with buccal tapes.

2. Description of the Related Art

Various treatments and products are in use for the relief of irritations identified with canker sores and the like. Most of these products are intended to relieve the pain associated with these irritations and to shorten the duration of the source of these irritations.

Typically, these products are in the form of ointments and solutions for topical application, or in a suitable formulation for a mouthwash. For the treatment of canker sores, these products have variously employed ingredients such as astringents of which alum and tannic acid are examples; demulcents of which benzoin is an example; counterirritants, of which camphor and menthol are examples; anesthetics, such as benzocaine; germicides; and antiseptics. Some of these products are formulated so as to provide a gel base which forms a protective coat about the source of irritation and thereby reduces the pain caused by the simple mechanical action of, illustratively, a tooth rubbing against a sore. Another type of product employed is silver nitrate in sticks to cauterize canker sores in the mouth.

Still another approach to the treatment of canker sores has employed tetracycline or oxytetracycline in two topical modes of delivery. One such mode consists of washing the oral cavity with a tetracycline suspension (5 ml., 250 mg/ml.) for 3-5 minutes, 4-5 times daily, for about five days. The medication is then swallowed or expectorated. The second mode involves applying a gauze compress saturated with 250 mg tetracycline in 30 ml. of water. Others have also employed the same amount of cephalexin monohydrate in a gauze compress in place of tetracycline. These modes of delivery, however, require that the patient refrain from eating or drinking for one hour following administration in order to enhance therapy. Moreover, due to the recurring nature of canker sores, the treatment requires frequent use of large amounts of antibiotic and antibiotic-like drugs. Such use, it is well known, often leads to the acquired resistance to such drugs and to potentially severe and threatening allergic reactions.

Systemic treatment with tablet or capsule doses of antibiotics and/or steroids have also been employed in the treatment of canker sores and the like. However, this form of therapy is not preferred and is generally employed in only severe and frequently recurring cases.

A more complete description of the above discussed treatments and others may be found in U.S. Pharmacist, February 1978, pages 36-48; Arch. Dermatol. (Vol. 109, 400-402 (1974); Oral Surg., Vol. 30, No. 4, 476-487 (1970); and U.S. Pat. No. 4,117,120. The present invention relates to a new method of treating irritations identified with aphthous stomatitis and the like which is not disclosed in, nor rendered obvious by, any of the above cited publications, nor elsewhere in the art.

SUMMARY OF THE INVENTION

According to the present invention, a method of treatment is provided for the relief of the discomfort associated with canker sores and like lesions of the mucous membranes. The method comprises topical application of tape dosage forms containing minor amounts of at least one topically effective antibiotic-, antibacterial-, antimicrobial-, anti-infective- and antiviral-like agents. Preferably these tape dosage forms are of the type which cover the infected area but effectively isolate the active ingredient from the remainder of the surrounding environment.

Minor amount in this application, means the minimum therapeutically effective amount up to about 15 mg.

DETAILED DESCRIPTION OF THE INVENTION

This invention relates to a method of treating aphthous stomatitis, sores, lesions and blisters affecting the mucous membranes. The method comprises topical application of tape dosage forms containing minor amounts of topically effective antibiotic-, antibacterial-, antimicrobial-, anti-infective and antiviral-like agents to the affected area.

Canker sores, known also as aphthous ulcer, are recurrent sores that form on a patient's inner cheek, lips, gums, tongue or soft palate. The condition is medically known as aphthous stomatitis. While the sores are not life threatening, they are usually painful and bothersome to the patient. The severity of the condition, the number of sores and the frequency of recurrence varies from individual to individual. Recent clinical findings indicate that a pleomorphic alpha-hemolytic streptococcus, streptococcus sanguis, strain 2A, may be the cause of the condition.

According to the method of this invention, effective relief from the irritation caused by these sores, lesions, blisters, ulcers and the like affecting the mucous membrane is obtained with topical application of tape dosage forms containing minor amounts of the topically effective active agents. More particularly, each tape dosage form may contain from about 1 mg. to about 15 mg. of the active agent, and preferably from about 1-2 mg. to about 5 mg. The tape dosage forms of this invention have been used to treat volunteer patients. Thus, the dosage form of this invention has been applied to affected areas of the mucous membrane of patients suffering from canker sores for ½ an hour up to 8 hours, 1 to 4-5 times a day, for 1 to 3 days. In each case the patient responded well to the treatment with healing in 2 to 3 days after onset of treatment.

In this invention, a tape dosage form refers to a self-contained medicated bandage capable of adhering to the surfaces found in the mucousal cavity. Preferably, such a tape will be constructed so as to substantially isolate the active ingredient from the areas adjacent to its application. This isolation can be achieved by localizing the active ingredient in a central portion of the tape, the adjacent surfaces of which form an adhesive border around the active ingredient; or by incorporating the active ingredient within the adhesive area itself.

Useful tape dosage forms will vary depending on the site of administration and many types are well known to those skilled in the art. The tape dosage forms for the mucous membranes are those known as buccal tapes. The buccal tapes which are preferably employed in this invention are of the type described in U.S. Pat. No. 3,972,995, granted Aug. 3, 1976, the disclosure of which is hereby incorporated by reference in its entirety. Tapes of the type therein disclosed are preferred since those dosage forms not only maintain the drug in direct and intimate contact with a limited area of the oral mucosa but also isolate the drug from the rest of the oral cavity, thereby preventing the drug from being influenced or carried away by the normal secretions of the oral cavity, and allowing essentially normal functioning of the oral cavity during maintenance of the drug contact with said mucosa. Thus, said buccal tapes provide the feature of preventing the active ingredient from entering the gastrointestinal tract during administration.

A particular tape dosage employed in the method of this invention was prepared as generally described in Example II of the above noted U.S. Pat. No. 3,972,995, with the following modifications.

More specifically, the tape useful in the method of this invention can be made with a backing layer formed by spreading a solution of ethylcellulose (Ethocel Standard, 45 cps, Dow Chem. Co.) 1 part, and castor oil U.S.P. 1 part, in 4 parts of methylethyl ketone onto a glass plate and allowing the solvent to evaporate. The backing layer is about 5 mils thick and increases the limpness of the laminate. A second layer (up to 1 mil in thickness) is deposited on the top of the backing, by spreading a solution of 1 part of Butyl Rubber 007 (Exxon Chemical Co.) in 3 parts n-heptane over it. An adhesive layer is deposited on top of the second layer by spreading a slurry over it. Typically, such a slurry comprises 10 parts of Karaya gum, superfine XXXX (Meer Corp.) which is slurried shortly before the spreading operation into 10.5 parts of a binder solution containing 15.85 percent by weight each of polyethyleneglycol 400 and polyvinylpyrrolidone (K-30), in ethanol. After spreading and evaporation of solvent, the tape is ready for introduction of the active ingredients.

The method of applying the medicament or active agent to the tape dosage form is well known to those skilled in the art and illustratively includes for buccal tape dosage forms-incorporation into the adhesive layer; spreading powder medicament through a mask; or spraying of solutions, slurries or powders of the drug onto the tape dosage form with or without a mask.

Individual tape dosage forms can be sized to accomodate the size of the sore, blister or the like under treatment, but are preferably sized in a rounded rectangular configuration. Accordingly, the minor amount of topically effective active ingredient will be contained in tape dosage having a surface area ranging from about $(3-5 \text{ mm})^2$ to about $(10-25 \text{ mm})^2$.

Drugs useful in the present invention include topically effective antibiotic, anti-bacterial, antimicrobial, antiviral and anti-infective agents. Selection of a particular agent will depend on the type or source of irritation treated. Illustratively when treating canker sores with antibiotics, an antibiotic effective against gram positive bacteria or a broad spectrum antibiotic would be selected. Drugs useful in the present invention illustratively include penicillins, cephalosporins, tetracyclines, erythromycin, and the like; trifluorothymieine, idoxuridine, and the like; and iodine, mafenide acetate, paraben esters, benzalkonium chloride and the like. In addition to the various active agents above discussed, the tape dosage form of this invention may additionally contain small amounts of other agents such as anesthetics which provide a form of immediate relief from the discomfort of the irritation and during healing.

Accordingly, by the method of this invention, it has been found that over 70% of the volunteers participating, have obtained fast healing and relief from the described irritations. Further, it appeared that even those subjects who did not respond would have responded favorably with proper selection of active agent.

The method of treatment of this invention can also be used for treating herpes simplex labialis and the sores, lesions, blisters and the like incident to that viral infection.

The invention is further illustrated but not limited by the following examples.

EXAMPLE 1

Subject I contracts canker sores 5-6 times per year, which sores require up to 14 days to heal with or without various standard treatments including the use of peroxide. The instant canker sore developed in the right inside cheek between the two rows of teeth. On the day following appearance of the canker sore, a single buccal tape containing 1.7-2.2 mg. of erythromycin base hydrate was applied and left in place for 1 hour. A second buccal tape containing the same medicament and dose as the first tape was applied 3 hours following the first application and left in place for 2 hours. On the day following the onset of treatment the sore had healed.

EXAMPLE 2

Subject II experiences canker sores 5-6 times per year, which sores require up to 14 days to heal with or without treatment. Previous treatments employed by Subject II included peroxide, alum, tannic acid, a combination of benzocaine-phenol-iodine in alcoholic solution and a paste of triamcinolone acetonide. Subject II developed 2 canker sores: on the right buccal surface near the wisdom tooth and left buccal surface near the eye teeth. One buccal tape containing 1 mg. of erythromycin base hydrate was applied to each canker sore for 1½ hours and this application was repeated again 8 hours later on the same day. One canker sore had healed on the day following onset of treatment. The second sore received a third, 1 hour application of a 1 mg. erythromycin base hydrate buccal tape on the day following onset of treatment. The second sore was found to have healed on the second day following onset of treatment.

EXAMPLE 3

Subject III experiences canker sores on the average of once a month with healing requiring 2-3 days with or without treatment. Previous treatments employed alum. Subject III developed a canker sore on the inside lower lip and on the day of its appearance applied a single buccal tape containing 1 mg. of erythromycin base hydrate for 3 hours. Nine hours after the time of first administration (the next day), a second buccal tape containing the same dose as the first was applied for 50 minutes; and the sore was healed the same day, the first day after onset of treatment.

EXAMPLE 4

Subject III at a different time than in Example 3 developed a canker sore in the front inside upper lip. On the day following its appearance, a single buccal tape dosage was administered in the morning for 1 hour and a second tape in the evening for 2 hours. Both tapes contained about 2¼ mgs. of 3:1 tetracycline hydrochloride:lidocaine. The sores were healed on the first day following onset of treatment.

EXAMPLE 5

Subject IV experiences canker sores on the average of twice a month. The sores generally require 7-14 days to heal without treatment and 4-5 days with treatment. Subject IV developed a canker sore on the right lower gumline and began treatment on the second day following its appearance with application of a single buccal tape in the morning and a second in the evening each of which were left in place for 1½ hours. Each of the tapes contained 1 mg. erythromycin base hydrate. On the day following onset of treatment the sore was healed.

EXAMPLE 6

Subject IV, at a different time than in Example 5, contracted a canker sore on the top left gum in the back of the mouth. On the day following its appearance single buccal tape dosage forms containg 1.2-1.8 mg. of erythromycin base hydrate were applied separately in the morning and evening for 2 hours. On the day following onset of treatment the sores were healed.

EXAMPLE 7

Subject V experiences canker sores about 3 times per year, the sore generally taking 5-7 days to heal without any treatment and at best 2 days with treatment. Previous treatments included the application of a paste containing triamcinolone acetonide. Subject V developed a canker sore in the upper right portion of the mouth between the gums and the teeth. On the day following its appearance a single buccal tape containing 1 mg. of iodine was applied overnight for about 8 hours followed by a second application of a similarly dosed buccal tape for 4 hours. The sore was healed on the day following onset of treatment.

EXAMPLE 8

Subject VI experiences canker sores 3-4 times per year, the sores requiring about 14 days to heal without treatment. Previous treatments employed alum to no effect. This subject developed a canker sore on the edge of the lower lip and treated the sore on the day following its appearance with a single buccal tape for 3 hours and on the next day with a single buccal tape for 30 minutes. Both tapes contained 1.2-1.8 mg. erythomycin base hydrate. The sore was healed by the second day following onset of treatment.

EXAMPLE 9

Subject VI, at a time different than in Example 8, developed a canker sore on the inside of the upper lip. The sore was treated with buccal tapes containing 1 mg. iodine for 30 minutes each as follows; on the first day following the sore's appearance treatment began with 2 applications; on the fifth day, 4 applications; and on the sixth day, 3 applications. The sore was healed on the fourth day following onset of treatment.

EXAMPLE 10

Subject VII experiences canker sores on the average of 1-2 per month which sores require 14-18 days to heal without treatment and at best 2-4 days with treatment. Previous treatments included silver nitrate sticks, peroxide, alum, diethylether, and an alcoholic solution of benzocaine-phenol-iodine. The subject developed a canker sore on top of the tongue and commenced treatment with buccal tapes containing 1.5-2.0 mg. erythromycin base hydrate on the second day following the sore's appearance. On the first day of treatment a single tape was applied for 1½ hours; on the second day, one in the morning for 1½ hours and one in the evening for 2 hours; and on the third day, one tape for 2 hours. The sore was healed on the second day following onset of treatment.

EXAMPLE 11

Subject VII also developed a pair of canker sores on the inside lower lip very close to the lip ava at about the same time as in Example 10. The sores were close enough so as to permit the use of a single buccal tape. On the fourth day following appearance of the sore, treatment began with a buccal tape containing 1.5-2 mg. of erythromycin base hydrate as follows: On day 1 of treatment a buccal tape was applied at four times during the day for 1½ to 2 hours each. On the first day following onset of treatment (day 2) one sore had healed and the second sore was healing.

The sore area was reinjured on day 2 and treatment began again the next day (day 3) with the application of a buccal tape four times during the day at 2 hours for each application. On the next day (day 4) a single tape was applied for 1½ hours and after its removal the sore was found to be healing, however, it was then reinjured. Four more tapes were applied that day (day 4) for periods of 1½ to 2 hours. Five tapes were applied the next day (day 5) and three more in the morning and early afternoon of the following day (day 6). On that same day (day 6), the first day following reinjury two more tapes containing about 2 mg. of erythromycin glucoheptanoate were separately applied for 2 and 3 hours respectively. On the second day (day 6), following the last reinjury (day 4) the sore was found to be healed.

EXAMPLE 12

Four subjects did not immediately respond to treatment. Of these, 3 subjects were treated with tapes containing erythromycin base hydrate and 1 subject with a tape containing iodine. Only one of these volunteer subjects was treated again and at that time the subject responded well to treatment employing a buccal tape containing less than 2 mg. of tetracycline hydrochloride, which indicates that individual patients would be responsive to proper selection of the active ingredient.

What is claimed is:

1. A method of treating aphthous stomatititis, affecting mucous membranes of the mouth lips cheeks and gums of the oral cavity comprising topical application of tape dosage forms containing a therapeutically effective minor amount of at least one topically effective antibiotic, antibacterial, antimicrobial, antiinfective or antiviral active agent to the affected area wherein the active agent is localized in an area of the tape selected from either (a) the central portion of the tape, the adhesive surfaces of which form an adhesive border around the active agent, or (b) the adhesive layer of the tape.

2. The method of claim 1 wherein the minor amount is from about 1 milligram to about 15 milligrams.

3. The method of claim 1 wherein the minor amount is from about 1 milligram to about 5 milligrams.

4. The method of claim 1 wherein said tape dosage form is a buccal tape.

5. The method of claim 1 wherein said tape dosage form substantially isolates the active agent from the areas adjacent to its application.

6. The method of claim 1, 2, 3, 4 or 5 in which the surface area of tape dosage form is from about 9 square millimeters to about 625 square millimeters.

* * * * *